(12) United States Patent
Tanaami

(10) Patent No.: US 6,458,545 B2
(45) Date of Patent: Oct. 1, 2002

(54) BIOCHIP

(75) Inventor: Takeo Tanaami, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 09/784,799

(22) Filed: Feb. 15, 2001

(30) Foreign Application Priority Data

Feb. 22, 2000 (JP) ......................................... 2000-044384

(51) Int. Cl.⁷ .............................. C12Q 1/68; C12M 1/36; C12N 11/16; G01N 33/551
(52) U.S. Cl. ...................... 435/6; 435/174; 435/283.1; 435/287.2; 435/287.5; 435/288.5; 422/68.1; 422/81; 436/524
(58) Field of Search ........................ 435/287.2, 287.5, 435/283.1, 288.5, 6, 174; 422/68.1, 81; 436/524

(56) References Cited

U.S. PATENT DOCUMENTS 6,017,696 A * 1/2000 Heller et al. .................... 435/6
6,218,126 B1 * 4/2001 Yasuda et al. ................. 435/6

OTHER PUBLICATIONS

Wilding et al. "Integrated Cell Isolation and Polymerase Chain Reaction Analysis Using Silicon Microfilter Chambers" Analytical Biochemistry, 1998, 257:95–100.*

* cited by examiner

Primary Examiner—Stephanie W. Zitomer
Assistant Examiner—BJ Forman
(74) Attorney, Agent, or Firm—Moonray Kojima

(57) ABSTRACT

A biochip which is extremely safe and enables reduction of cost of testing and which comprises in sequence from opening of a blood collecting tube thereof: a collection block for retaining collected blood; a preprocessing block for deriving a target from the collected blood; and a substrate on which probes are deposited in arrays and the opening is closed airtight with a rubber plug.

12 Claims, 6 Drawing Sheets

BIOCHIP

BACKGROUND OF THE INVENTION

1. Field of Invention

This invention relates to a biochip for testing such substances as DNA, RNA or protein; and, more particularly, to a biochip that is safe and reduces cost of testing.

2. Description of the Prior Art

A biochip, such as a DNA chip, comprises several thousand to several hundred thousand types of known DNA segments, also referred to as DNA probes, deposited in a plurality of arrays on a substrate. If a solution containing an unknown DNA segment, also referred to as a DNA target, is caused to flow onto such a DNA chip, DNA segments of the same type combine with each other. This property is utilized so that a DNA probe, wherein such combination has taken place, is examined using a biochip reader, and thus, the sequence of the DNA target, for example, is determined.

FIG. 1 shows an example of hybridization seen in a biochip, wherein six DNA probes DN01, DN02, DN03, DN04, DN05 and DN06 are deposited in a plurality of arrays on a substrate SB01, thus forming a DNA chip. A DNA target UN01 is previously marked with a fluorescent marker LM01. When hybridized to the DNA chip, the DNA target combines with a DNA probe whose sequence is complementary. For example, the DNA target UN01 combines with DNA probe DN01, as indicated by CB01. Using a biochip reader, excitation light is irradiated at the DNA chip, thus hybridized, in order to detect fluorescent light produced at the fluorescent marker. Hence, it is possible to know which of the DNA probes the DNA target has combined with. For example, in an image SI01 resulting from scanning a DNA chip, fluorescent light is observed at the spot LD01 whereat the DNA combination CB01 was produced.

FIG. 2 shows a DNA chip as the biochip, wherein the biochip comprises a substrate 1, on which known DNA segments are deposited in a plurality of arrays (referred to as "substrate 1"); a cartridge 2 wherein the substrate 1 is housed and to which a solution containing a DNA target previously marked with a fluorescent marker is introduced; and an inlet opening 3 formed on cartridge 2 through which a solution is introduced. Cartridge 2 comprises a material which is permeable to both excitation light and fluorescent light produced thereby at the marker. Cells CL11, CL12, CL13, CL14, CL15 and CL16, in each of which a plurality of DNA probes of the same type are placed, are deposited in arrays on substrate 1.

The method of testing DNA or other substance using the biochip of FIG. 2 is described with reference to FIGS. 3 and 4, wherein FIG. 3 shows an example of introducing solution into cartridge 2, and FIG. 4 shows art example of scanning a hybridized DNA chip using a biochip reader to determine the sequence of target DNA, for example. FIG. 3 shows components 1 to 3 which are the same as those in FIG. 2.

In a first step, blood is collected using a syringe from a person being tested. A solution that was preprocessed is then introduced through an inlet opening 3 into cartridge 2. Solution infusion means or device 4, such as a pipette, is loaded with a preprocessed solution 5. The tip of solution infusion device 4 is inserted in inlet opening 3 and solution 5, inside the device 4, is injected into cartridge 2. The preprocessing refers to a series of processes wherein lymphocytes are separated from the collected blood, and then DNA is extracted from the separated lymphocytes, and finally, the extracted DNA is marked with a fluorescent marker.

In a second step, substrate 1 is soaked with solution introduced into cartridge 2 to allow a DNA target in the solution to hybridize with DNA probes placed in each cell on substrate 1.

In a final step, as shown in FIG. 4, hybridized substrate 1 is scanned using a biochip reader 50 so that, for example, the sequence of the DNA target is determined.

In FIG. 4, components 1 to 3 and cells CL11, CL12, and CL13 are similarly denoted as in FIG. 3. In addition, light emitted from a light source 6, such as a laser light source, is reflected by a dichroic mirror 7, as excitation light and focused through an objective lens 8 onto cells on substrate 1. For example, excitation light is focused onto cell CL12 in FIG. 4. Fluorescent light produced at cell CL12 on substrate 1 becomes parallel light at it travels through objective lens 8 and is projected onto dichroic mirror 7. The fluorescent light, thus projected, is transmitted through dichroic mirror 7. The fluorescent light thus transmitted then travels through a filter 9 and is condensed onto an optical detector 11 by a lens 10.

The spots, whereon excitation light is focused, are scanned by a drive means (not shown). For example, cartridge 2 or biochip reader 50 itself is scanned so that excitation light is irradiated at the remaining cells CL11 and CL13 on substrate 1. Hence, it is possible to determine the sequence of a-DNA target by identifying the position of a cell on substrate 1 where fluorescence takes place.

Recently, however, test samples, such as blood, have been found to be contaminated with a virus, such as HIV. Hence, there is a growing tendency, for safety reasons, to not recycle various medical devices, such as syringes, for cleaning or sterilization. Instead, disposable devices are preferred. In contrast, the method of introducing a solution, such as shown in FIG. 3, involves the risk of the human operator or testor becoming infected by a virus, such as HIV, as result of accidental contact with the solution. This risk is due to the transfer of the solution from the solution infusion device 4, or the like to cartridge 2.

Another problem is that the cost of testing is substantial since more than one type of medical equipment or device must be disposed of, including syringes, devices and appliances used for preprocessing purposes, solution infusion devices, DNA chips, etc.

SUMMARY OF THE INVENTION

Accordingly, an object of the invention is to overcome the aforementioned and other deficiencies, disadvantages, and problems of the prior art.

Another object is to provide a biochip which is extremely safe and enables great reduction in cost of testing.

The foregoing and other objects are attained in the invention, which encompasses a biochip collection means for retaining collected blood; preprocessing means for deriving a target from the collected blood; and substrate means on which probes are deposited in arrays with the opening thereto being air tight.

DETAILED DESCRIPTION OF PREFERRED EMBODIMENTS

Figure 1:
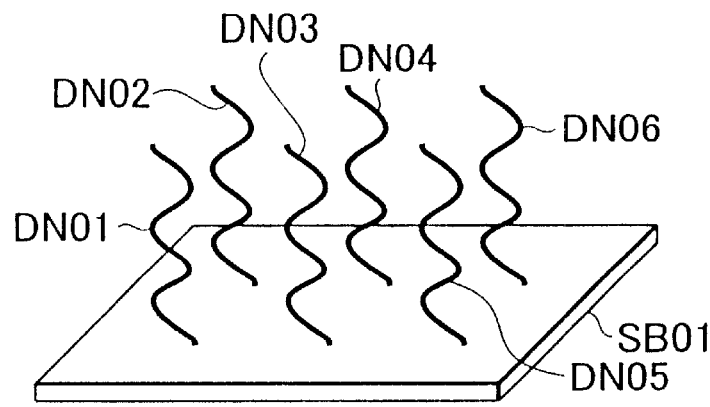
FIG. 1 is a schematic view depicting a prior art example of hybridization seen in a biochip.
Figure 1:
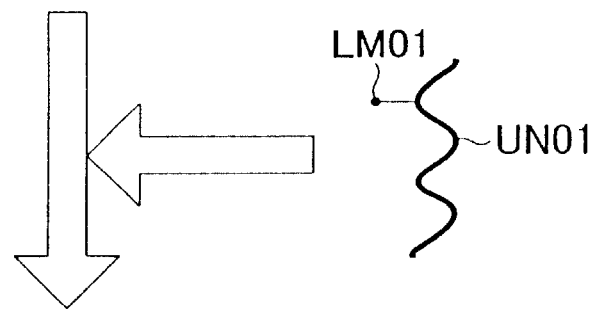
Figure 1:
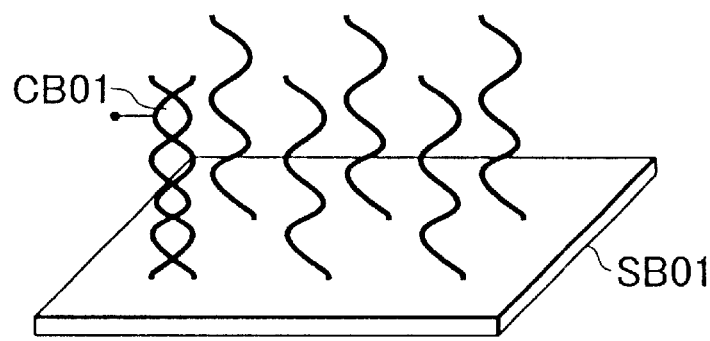
Figure 1:
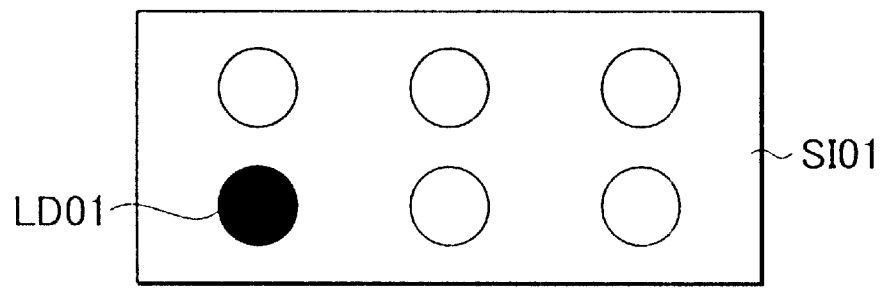
Figure 2:
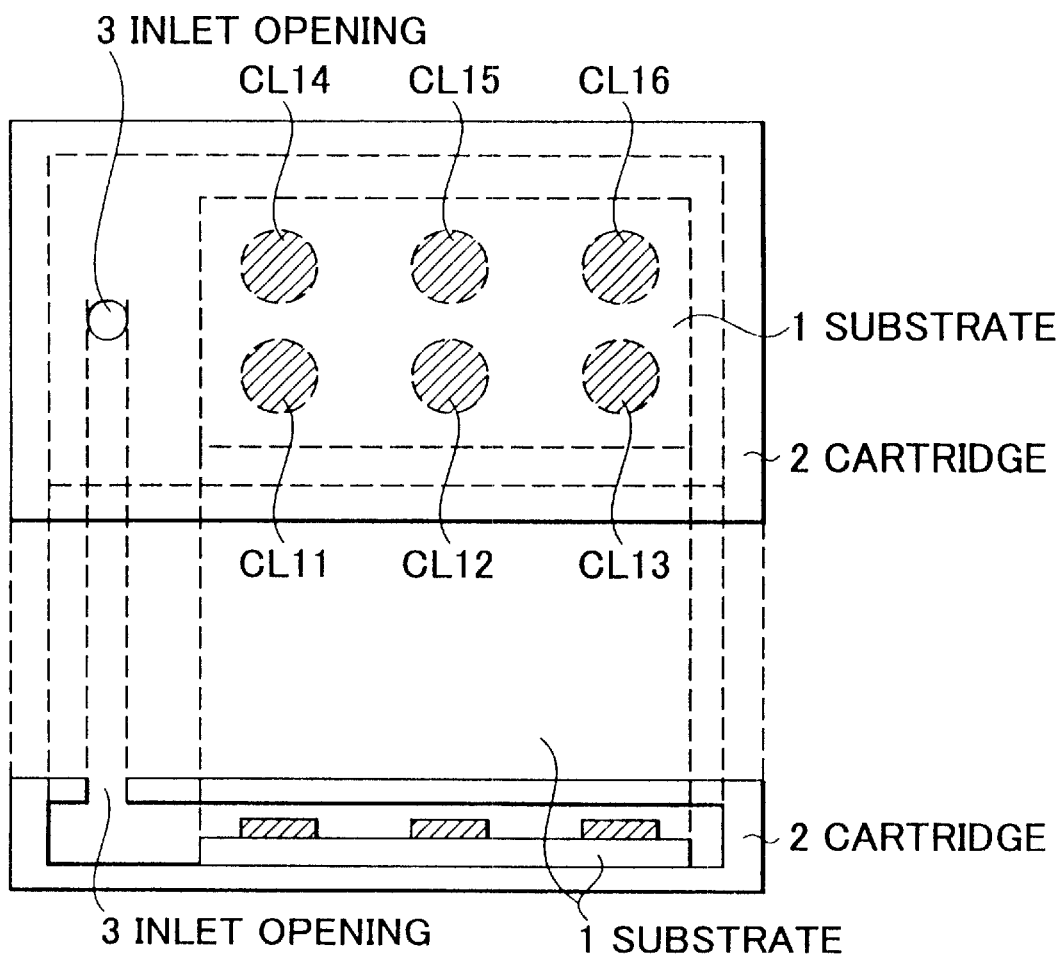
FIG. 2 is a schematic top, cross-sectional view depicting a prior art biochip.
Figure 3:
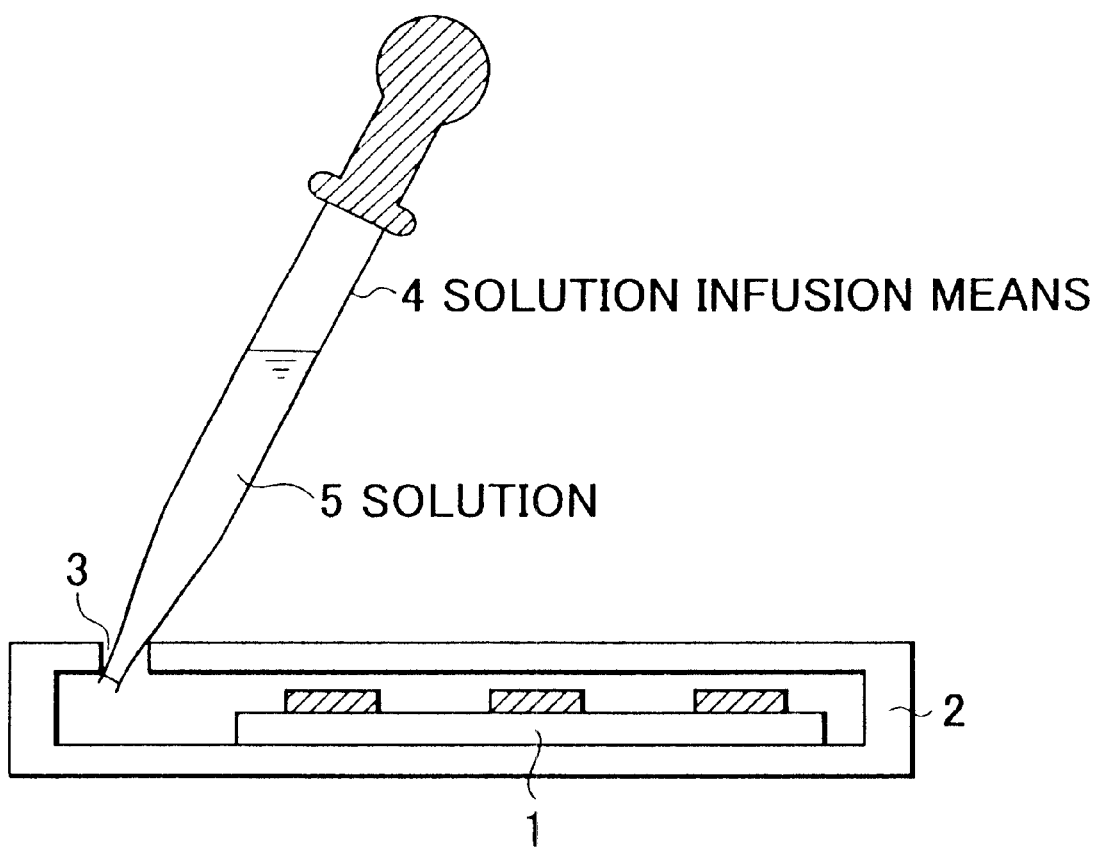
FIG. 3 is a schematic view depicting introduction of a solution into a cartridge.
Figure 4:
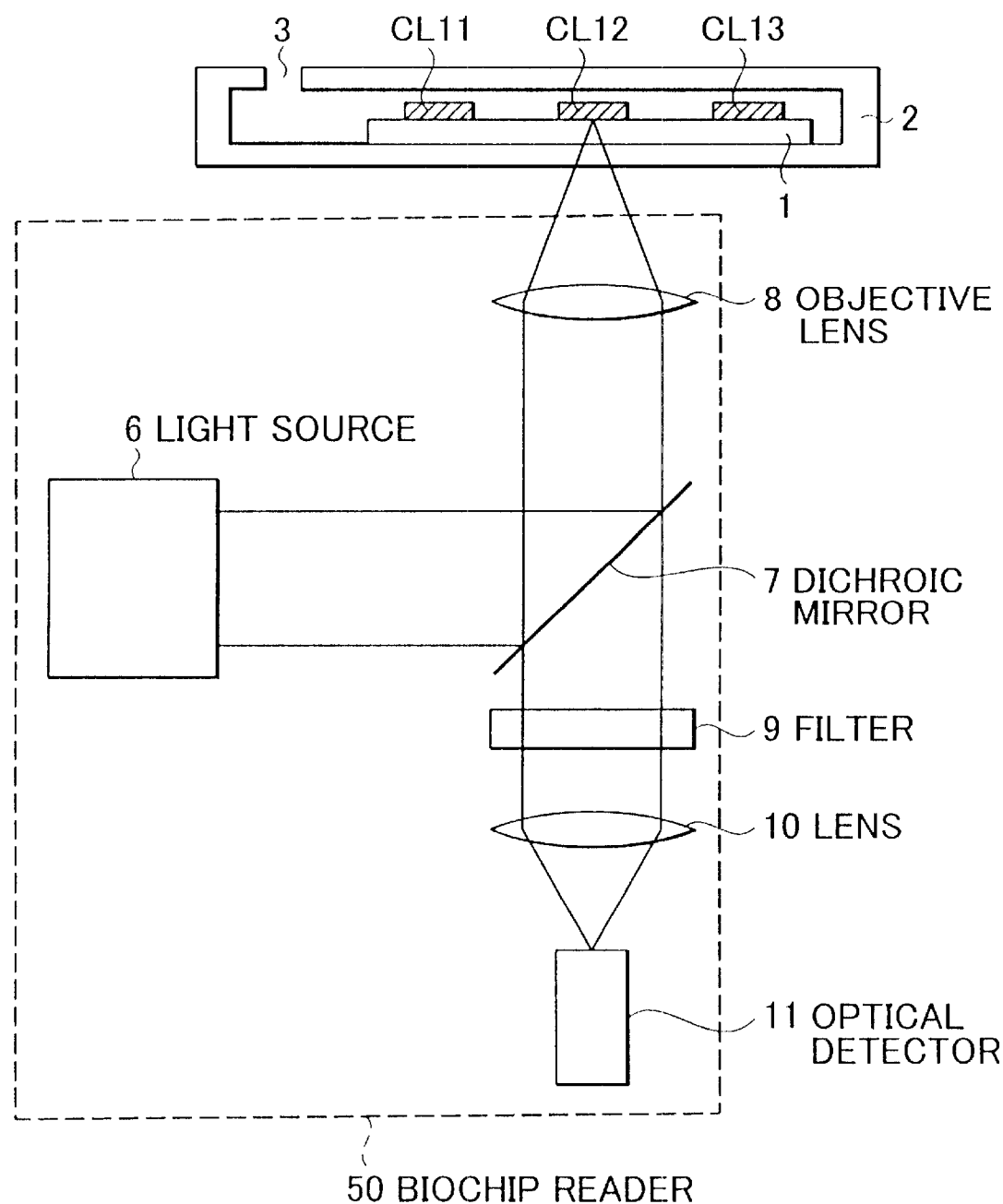
FIG. 4 is a schematic view depicting scanning of a hybridized DNA chip using a biochip reader to determine sequence of target DNA.
Figure 5:
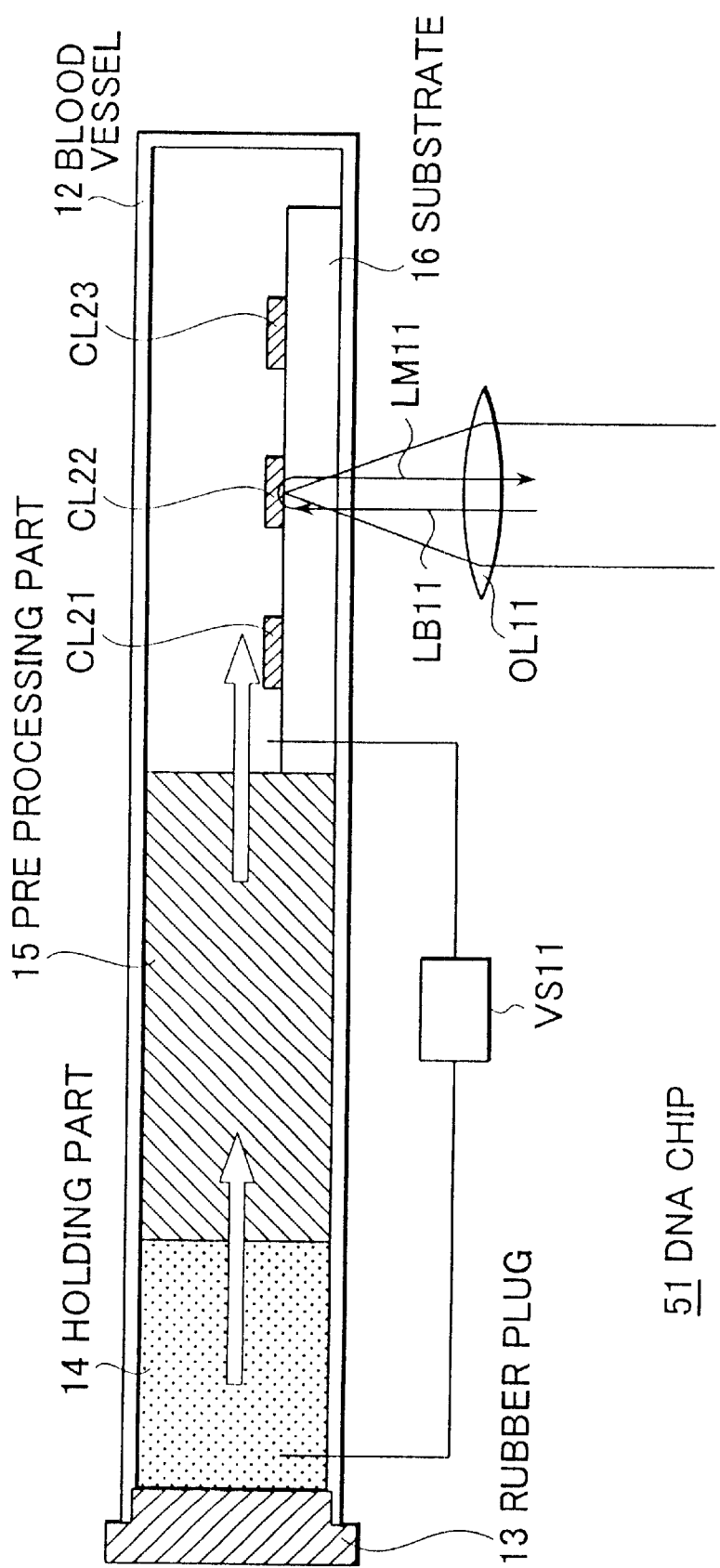
FIG. 5 is a cross-sectional view depicting an illustrative embodiment of the invention.

FIG. 5 shows a DNA chip (also called a biochip) 51 comprising a blood collecting tube 12, instead of a conventional split tube, which is inserted in a syringe cylinder in order to collect blood and is permeable to excitation light and fluorescent light produced thereby at a fluorescent marker. A substrate 16, on which DNA probes are deposited in arrays as samples (called "substrate 16) is disposed in the innermost section (see right end area) of blood collecting tube 12. Also, a preprocessing block 15, wherein the preprocessing previously described above, is carried out, is disposed in the intermediate section (see middle area) of blood collecting tube 12. Space in the outermost (see left end area) of blood collecting tube 12 serves as a collection block 14 for temporarily storing collected blood. The innermost section of tube 12 is kept under negative pressure against collection block 14 or is kept under vacuum, for example, and a rubber plug 13, whose middle area has a thin wall through which a needle can pierce, is disposed within the opening of tube 12 in order to make the tube air tight.

Cells CL21, CL22, CL23, each having a plurality of DNA probes deposited therein are disposed in a plurality of arrays on substrate 16 as shown in FIG. 5.

Figure 6:
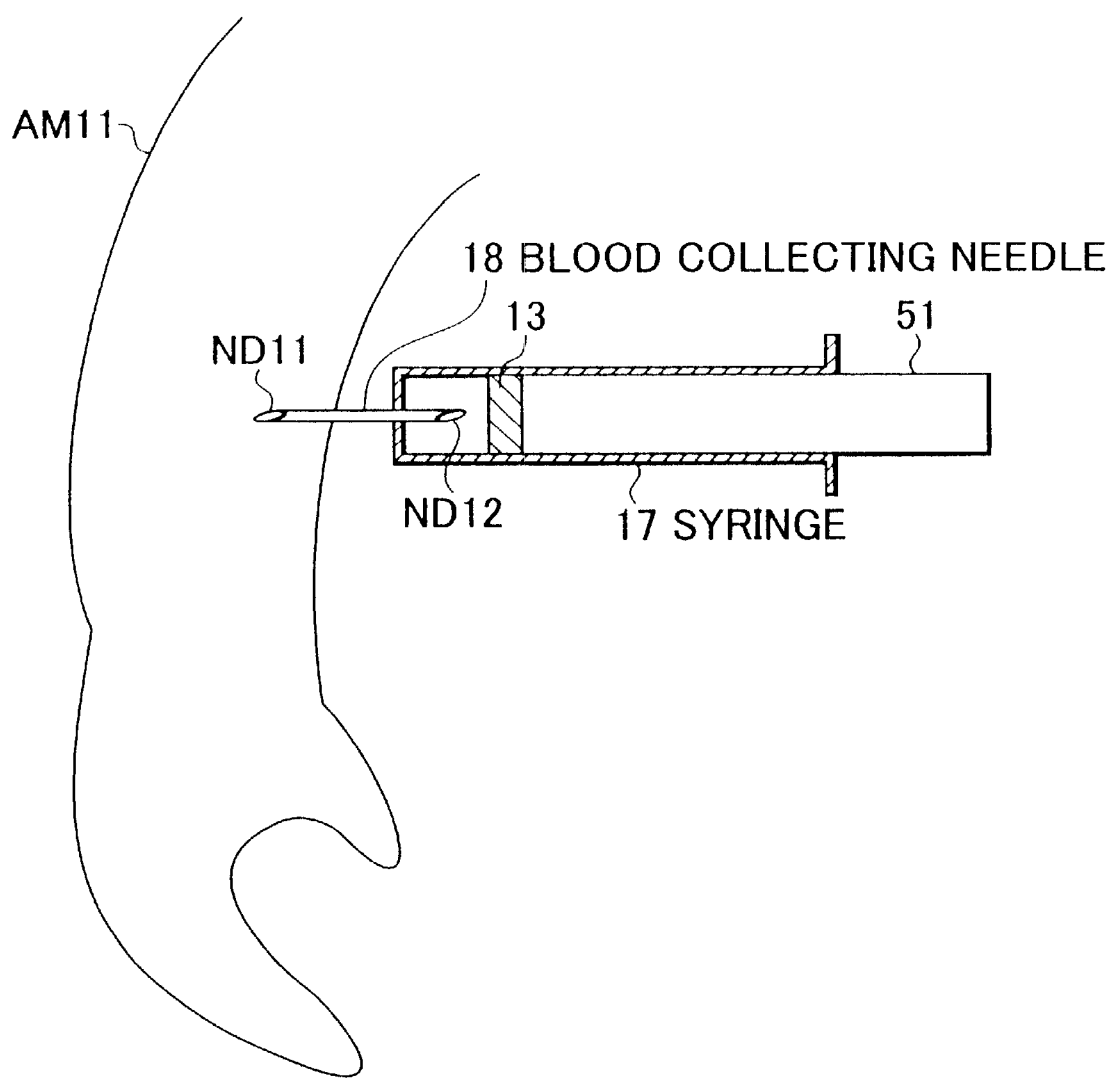
FIG. 6 is a schematic view depicting application of the invention.

The embodiment of FIG. 5 will now be described with regard to application and operation with reference to FIG. 6, wherein rubber plug 13 and DNA chip 51 are shown. A blood collecting needle 18 is disposed on the side opposite to the opening of syringe 17 and has two pierceable ends on opposite ends thereof, and labeled ND11, ND12. Instead of a split conventional tube, a DNA chip 51 is inserted through the opening of syringe 17. At this point, one end ND12 of needle 18 pierces through the middle area of rubber plug 13 on DNA chip 51 so that the end of the needle 18 is connected to DNA chip 51 As shown in FIG. 6, an arm AM11 of a person being tested is pricked with the other end ND11 of needle 18. Hence, blood is collected through needle 18 into collection block 14 of FIG. 5, for example, but not shown in FIG. 6, of DNA chip 51 so that blood collection is provided.

After blood is collected, blood collection needle 18 is removed from the arm AM11 of the patient and DNA chip 51 is removed from syringe 17. At this point, a pin hole, at a point in rubber plug 13, whereat needle ND12 pierced the plug 13, automatically closes due to the elasticity of the rubber plug 13, so that the blood collecting tube 12 is maintained air tight.

The collected blood in collection block 14 is then caused to infiltrate toward the innermost section of tube 12 under negative pressure against collection block 14 (see FIG. 5). Thus, blood is introduced into preprocessing block 15., whereat a series of processes are carried out, such as, for example, lymphocytes are separated from the collected blood, DNA is extracted from the separated lymphocytes, and the extracted DNA is marked with a fluorescent marker, as described hereinbefore.

The preprocessed DNA is caused to infiltrate rightward into the innermost section of blood collecting tube 12, under negative pressure exerted against collection block 14. The collected blood is thus introduced into the right end area section where substrate 16 is located. Then, a DNA target, marked with a fluorescent marker, is hybridized with DNA probes so that DNA segments whose sequences are complementary combine with each other.

Moreover, excitation light is irradiated at substrate 16, thus hybridized, using the biochip reader discussed before, and fluorescent light, produced at the fluorescent marker, is detected. Hence, it is possible to determine which of the DNA probes, the DNA target has combined with. For example, the excitation light of a biochip reader (not shown) indicated by LB11 in FIG. 5, is focused with an objective lens OL11 onto a cell CL22 on substrate 16. Then,by detecting fluorescent light LM11 produced at cell CL22, the DNA target is identified.

Then, upon completion of the testing, advantageously, all that remains to be done is to dispose of syringe 17 and DNA chip 51. In contrast, with the prior art devices and methods, a larger number of devices and equipment must be disposed of, such as those devices used for preprocessing, and solution infusion devices. Hence, advantageously, with the invention, a substantial cost reduction is attained for testing.

The biochip of the invention also eliminates the need for a human operator to transfer the collected blood to the DNA chip. Hence, with the invention, the human operator avoids the risk of being infected with a virus, such as HIV, as a result of accidental contact with the collected blood. Thus, with the invention, safety is enhanced.

Accordingly, the biochip of the invention comprising a blood collecting tube 12, which includes a collection block 14, a preprocessing block 15, and a substrate on which probes are deposited in arrays, is safe to use and reduces by a considerable amount the cost of testing.

Although a DNA chip is described as the biochip in the discussion of FIGS. 5 and 6, the invention is not so limited. The biochip may be of such types as an RNA, protein, or sugar chain samples deposited in arrays on a substrate.

In the case of RNA chips, the RNA samples undergo hybridization similar to the DNA samples, whereas the protein samples are submitted to an antigen-antibody reaction. In either case, a probe acts to combine with a target.

Also, the area where substrate 16 is located, is maintained under negative pressure against collection block 14 to enable introducing of a test sample of blood from collection block 14 to the preprocessing block 15. However, the invention is not limited to such a method.

One alternative method is to form electrodes on both ends of preprocessing block 15 and applying a voltage externally thereacross, so that blood, or the like, is introduced by electrophoresis. For example, DNA is introduced in a direction from preprocessing block 15 to substrate 16 when the polarities of a voltage source VS11 (in FIG. 5) are such that substrate 16 side (right) of voltage source VS11 is positive and the collection block 14 side (left) is negative. This is due to the fact that the DNA is negatively charged when the biochip is a DNA chip.

Another alternative method is to simply use natural diffusion caused by osmotic pressure to introduce blood or the like.

A further alternative method is to provide innermost section (right end area) of tube 12 with an evacuation port so as to evacuate the innermost section externally and hence introduce blood or the like by osmosis.

Although fluorescent light detection, using a fluorescent marker, is applied in the embodiment of FIG. 5, an alternative method can be used to detect electric current changes corresponding to hybridization or by conducting mass analysis. In the method based on electric current changes, for example, a molecule known as an inter-currenter is slipped into a double chain after hybridization. Then, an electric current is measured since it only flows through the electrodes where hybridization has taken place. In the case of mass analysis, ionized DNA molecules picked from each cell are moved in a vacuum and the moledular weight thereof is determined from the difference in time each DNA molecule arrives at a given electrode.

The invention enjoys the following and other advantages. The invention comprises a collection block, a preprocessing block, and a substrate on which probes are deposited in arrays, all disposed in a blood collecting tube whereby need for a human operator to transfer the collected blood to a biochip is eliminated so that risk of being infected with a virus, such as HIV, as a result of accidental contact with the collect blood is substantially eliminated and hence safety is enhance.

Another advantage is that after completion of testing, only the syringe and biochip need be disposed of. In contrast, the prior art requires disposal of multiplicity of devices and equipment, such as those used for preprocessing and solution infusion. Hence, advantageously, the invention provides a simple testing method which is inexpensive.

According to an aspect of the invention, a preprocessing block derives DNA from blood collected in a collection block. Then, since samples deposited in arrays on a substrate are also samples of DNA, a DNA probe and a DNA target, whose sequences are complementary, combine with each other as a result of hybridization. Hence, it is possible with the invention to readily and simply determine the sequence of the DNA target.

According to another aspect of the invention, a preprocessing block derives RNA from blood collected in a collection block. Then, since samples deposited in arrays on the substrate are also samples of RNA, an RNA probe and an RNA target whose sequences are complementary combine with each other as a result of hybridization. Hence, it is possible with the invention to determine simply and reliably the sequence of the RNA target.

According to a further aspect of the invention, a preprocessing block derives protein from blood collected in a collection block. Then, since samples deposited as arrays on a substrate are also samples of protein, a protein probe and a protein target whose sequences are complementary combine with each other as a result of antigen-antibody reaction. Hence, it is possible with the invention to simply and reliably determine the sequence of the protein target.

The foregoing description is illustrative of the principles of the invention. Numerous extensions and modifications thereof would be apparent to the worker skilled in the art. All such extensions and modifications are to be considered as part and parcel of the invention.

What is claimed is:

1. A disposable device comprising a biochip fittable into an elongated cylindrical syringe having a blood collecting tube at one end thereof, said disposable device comprising:
   a plug;
   holding means for retaining collected blood;
   preprocessing means for deriving a target molecule from said collected blood; and
   substrate means on which probes are deposited in arrays; wherein
      said disposable device is fitted into said syringe so that a needle is inserted through said plug into said holding means during blood collection, and withdrawn from said plug after said blood collection causing said holding means to become closed air tight following blood collection; and wherein
      said disposable device is removed from said syringe after blood collection.

2. The disposable device of claim 1, further comprising means for causing diffusion of said collected blood from said holding means into said preprocessing means.

3. The disposable device of claim 1, further comprising means for providing negative pressure so that collected blood is introduced from said holding means into said preprocessing means by osmosis.

4. The disposable device of claim 1, further comprising means for providing depressurization and evacuation so that collected blood is introduced from said holding means into said preprocessing means.

5. The disposable device of claim 1, further comprising means for applying a voltage externally to said preprocessing means so that collected blood is introduced from said holding means into said preprocessing means by electrophoresis.

6. The disposable device of claim 1, wherein said preprocessing means derives DNA from said collected blood; and wherein said probes are also DNA.

7. The disposable device of claim 1, wherein said preprocessing means derives RNA from said collected blood; and wherein said probes are also RNA.

8. The disposable device of claim 1, wherein said preprocessing means derives protein from said collected blood; and wherein said probes are also protein.

9. The disposable device of claim 1, wherein said device further comprises an elongated cylinder replaceably fittable into said syringe, and wherein said plug is disposed at one end of said cylinder with said holding means disposed within said cylinder adjacent to said plug, and with said preprocessing meand disposed within said cylinder adjacent to said holding means, and wherein said substrate means is disposed within said cylinder adjacent to said preprocessing means and at another end of said elongated cylinder of said syringe.

10. The disposable device of claim 1, wherein said plug is of an elastic material so that said needle penetrates there-through when blood is collected, and when said needle is retracted after blood is collected, said plug becomes closed so that blood inside said holding means does not leak out.

11. The disposable device of claim 1, wherein said holding means, said preprocessing means, and said substrate means are contained serially within a single chamber.

12. A biochip comprising:
   a collecting tube having an airtight opening for collecting blood;
   collection means for retaining collected blood;
   preprocessing means for deriving a target from said collected blood;
   substrate means on which probes are deposited in arrays; and
   means for causing the collected blood to move to said collection means, to said preprocessing means, and to said substrate means, whereby collected blood is retained in a leakproof environment so as to protect an operator from exposure thereto.

* * * * *